US012672788B2

(12) United States Patent
Ebata

(10) Patent No.: US 12,672,788 B2
(45) Date of Patent: Jul. 7, 2026

(54) DETECTION DEVICE AND DETECTION SYSTEM

(71) Applicant: FUJITSU COMPONENT LIMITED, Tokyo (JP)

(72) Inventor: Kazuyoshi Ebata, Tokyo (JP)

(73) Assignee: FUJITSU COMPONENT LIMITED, Tokyo (JP)

( * ) Notice: Subject to any disclaimer, the term of this patent is extended or adjusted under 35 U.S.C. 154(b) by 82 days.

(21) Appl. No.: 18/234,618

(22) Filed: Aug. 16, 2023

(65) Prior Publication Data

US 2024/0164654 A1      May 23, 2024

(30) Foreign Application Priority Data

Nov. 17, 2022      (JP) ................................. 2022-184055

(51) Int. Cl.
*A61B 5/05*        (2021.01)
*A61B 5/00*        (2006.01)
*A61B 5/11*        (2006.01)
*G01S 7/35*        (2006.01)

(52) U.S. Cl.
CPC .............. *A61B 5/05* (2013.01); *A61B 5/1126* (2013.01); *A61B 5/7257* (2013.01); *G01S 7/356* (2021.05); *A61B 5/6893* (2013.01)

(58) Field of Classification Search
None
See application file for complete search history.

(56) References Cited

U.S. PATENT DOCUMENTS

| | | | |
|---|---|---|---|
| 8,428,696 B2 * | 4/2013 | Foo ..................... | A61B 5/02444 600/509 |
| 10,667,715 B2 * | 6/2020 | Rappaport ............... | A61B 5/05 |
| 2014/0058256 A1 * | 2/2014 | De Jong .............. | G01S 13/343 600/430 |
| 2020/0037890 A1 * | 2/2020 | Cho ................... | A61B 5/02444 |
| 2020/0037980 A1 | 2/2020 | Inomata | |
| 2020/0317207 A1 | 10/2020 | Sloushch et al. | |

(Continued)

FOREIGN PATENT DOCUMENTS

| | | |
|---|---|---|
| CA | 03180649 | 11/2022 |
| JP | 2021-74272 | 5/2012 |

(Continued)

OTHER PUBLICATIONS

European Search Report dated Nov. 22, 2023 in a counterpart European Patent Application No. 23191979.6.

(Continued)

*Primary Examiner* — Yi-Shan Yang
(74) *Attorney, Agent, or Firm* — STAAS & HALSEY LLP

(57)        ABSTRACT
A detection device includes a first sensor configured to transmit a first electromagnetic wave to a first range and receive the first electromagnetic wave reflected in the first range, a second sensor configured to transmit a second electromagnetic wave to a second range different from the first range and receive the second electromagnetic wave reflected in the second range, and a processor configured to calculate information on an object reflecting the first electromagnetic wave and the second electromagnetic wave based on a first signal output from the first sensor and a second signal output from the second sensor.

5 Claims, 11 Drawing Sheets

(56)                    References Cited

U.S. PATENT DOCUMENTS

2021/0128068 A1*    5/2021    Ghoshal ............. A61B 5/02444
2022/0099817 A1*    3/2022    Crouch ................. G01S 13/426

FOREIGN PATENT DOCUMENTS

| JP | 2017-131445 A | 8/2017 | |
| JP | 2020-74805 A | 5/2020 | |
| JP | 2020-531063 A | 11/2020 | |
| JP | 2022-25732 A | 2/2022 | |
| KR | 10-2020-0039135 A | 4/2020 | |
| KR | 2020039135 A * | 4/2020 | ............. B60N 2/002 |
| WO | 2022/075467 A1 | 4/2022 | |

OTHER PUBLICATIONS

Extended European Search Report issued on Dec. 8, 2025 in a counterpart European Patent Application No. 25198330.0.
Notice of Reasons for Refusal was issued on Mar. 24, 2026 in a counterpart Japanese Patent Application No. 2022-184055.

* cited by examiner

DETECTION DEVICE AND DETECTION SYSTEM

CROSS-REFERENCE TO RELATED APPLICATION

This application is based upon and claims the benefit of priority of the prior Japanese Patent Application No. 2022-184055 filed on Nov. 17, 2022, the entire contents of which are incorporated herein by reference.

FIELD

A certain aspect of the embodiments is related to a detection device and a detection system.

BACKGROUND

There is known an apparatus for detecting information on a living body of a passenger or the like in a vehicle. It is known that when a radar sensor is used as a sensor for detecting the information on the living body, the information on the living body is detected using an output signal of the radar sensor and an output signal of a vibration sensor. Note that the technique related to the present disclosure is disclosed in Patent Document 1 (International Publication Pamphlet No. WO2022/075467), Patent Document 2 (Japanese National Publication of International Patent Application No. 2020-531063), Patent Document 3 (Japanese Laid-Open Patent Publication No. 2022-25732), Patent Document 4 (Japanese Laid-Open Patent Publication No. 2020-74805) and Patent Document 5 (Japanese Laid-Open Patent Publication No. 2017-131445).

SUMMARY

It is an object of the present disclosure to provide a detection device and a detection system capable of improving a detection accuracy of information on an object.

According to an aspect of the present disclosure, there is provided a detection device including: a first sensor configured to transmit a first electromagnetic wave to a first range and receive the first electromagnetic wave reflected in the first range; a second sensor configured to transmit a second electromagnetic wave to a second range different from the first range and receive the second electromagnetic wave reflected in the second range; and a processor configured to calculate information on an object reflecting the first electromagnetic wave and the second electromagnetic wave based on a first signal output from the first sensor and a second signal output from the second sensor.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Hereinafter, a description will be given of the embodiment of the present disclosure with reference to the drawings.

Since a radar sensor for detecting biological information using millimeter wave radar or the like can detect the biological information without contacting a living body, a cable or sensor need not be attached to the body, and a burden on the body is small. However, in a case where the biological information is detected using the radar sensor in an environment with many vibrations such as a in the vehicle of automobiles, trains, and airplanes, for example, vibrations caused by vehicles other than the biological vibrations have a large influence. For this reason, even if an attempt is made to detect the biological vibrations of the passenger using the radar sensor, the passenger vibrates due to the vibration of the vehicle. Thus, a distance between the living body of the passenger and the radar sensor changes due to the vibration of the vehicle. Therefore, it is difficult to detect the biological vibrations. When the vibrations other than the biological vibrations are detected by the vibration sensor or the like as described in Patent Documents 1 and 2, the vibrations detected by the vibration sensor are different from the vibrations detected by the radar sensor, so that it is difficult to accurately remove the signals other than the biological vibrations from the output signal of the radar sensor.

In the following embodiment, a plurality of radar sensors are provided, the plurality of radar sensors detect vibrations in different ranges of the living body, and the biological information is calculated based on signals output from the plurality of radar sensors. Thus, vibrations other than the biological vibrations can be removed with high accuracy.

First Embodiment

Figure 1:
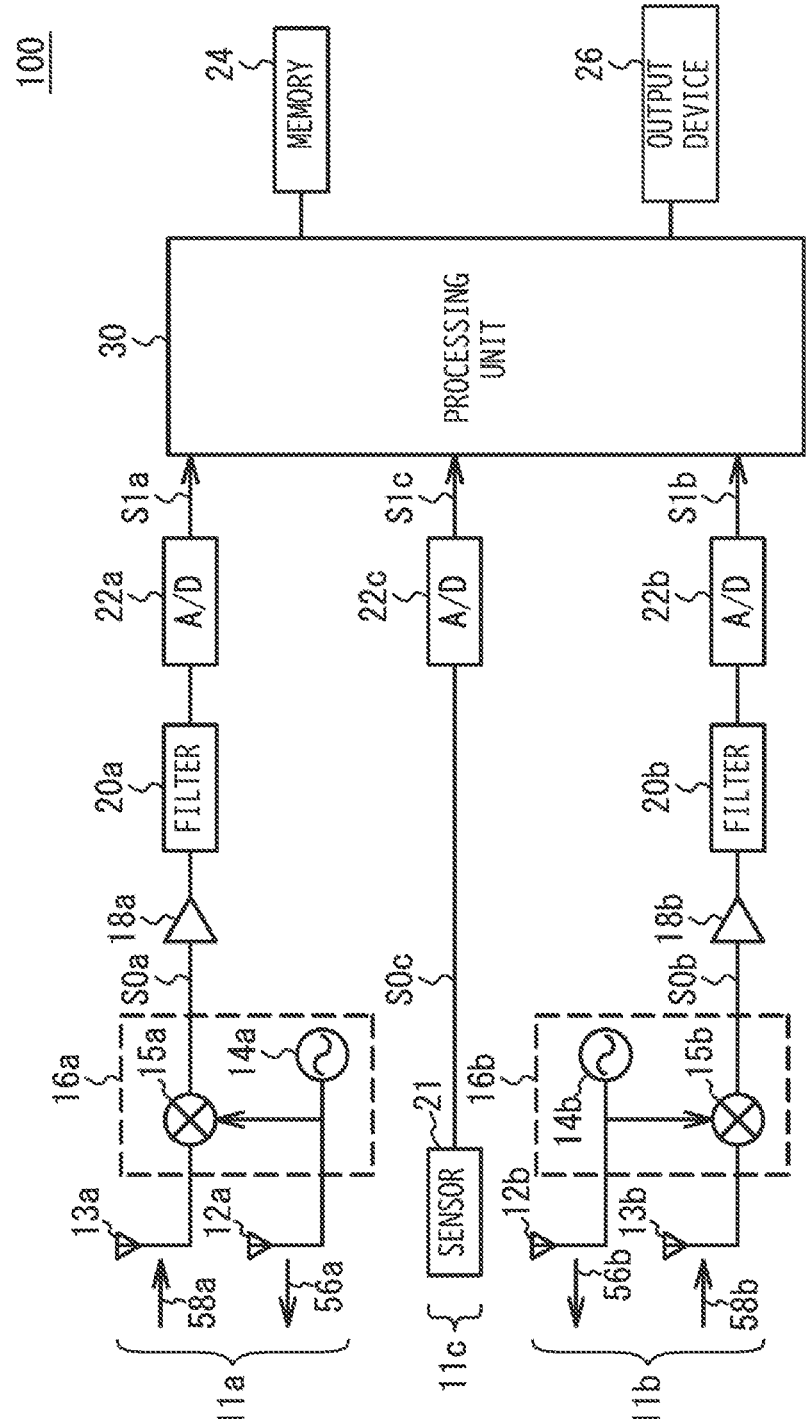
FIG. 1 is a block diagram illustrating a detection device according to a first embodiment.

FIG. 1 is a block diagram illustrating a detection device according to a first embodiment. A detection device 100 includes radar sensor units 11a and 11 b, a vibration sensor unit 11c, and a processing unit 30. The radar sensor unit 11a (and lib) includes an antenna 12a (and 12b) for transmission, an antenna 13a (and 13b) for reception, a high frequency circuit 16a (and 16b), an amplifier 18a (and 18b), a filter 20a (and 20b), and an Analog/Digital (A/D) converter 22a (and 22b). The vibration sensor unit 11c includes a sensor 21 and an A/D converter 22c.

In the radar sensor unit 11*a* (and 11*b*), the high frequency circuit 16*a* (and 16*b*) includes an oscillator 14*a* (and 14*b*) and a mixer 15*a* (and 15*b*). Although the high frequency circuit 16*a* (and 16*b*) is provided with an amplifier or the like, description thereof is omitted. The antenna 12*a* (and 12*b*) transmits a signal 56*a* (and 56*b*) generated by the oscillator 14*a*. The signals 56*a* and 56*b* are electromagnetic waves, such as microwaves or millimeter waves. The frequencies of the signals 56*a* and 56*b* are, for example, between 10 GHz and 120 GHz, and as an example, about 24 GHz. The antenna 13*a* (and 13*b*) receives a reflected signal 58*a* (and 58*b*) when the signal 56*a* (and 56*b*) is irradiated to the living body. The mixer 15*a* (and 15*b*) mixes the signals 56*a* and 58*a* (and 56*b* and 58*b*) and outputs a converted signal. The frequency of the signal S0*a* (and S0*b*) output by the mixer 15*a* (and 15*b*) corresponds to a difference between the frequency of the signal 56*a* (and 56*b*) and the frequency of the signal 58*a* (and 58*b*). Thus, the signal S0*a* (and S0*b*) becomes an analog signal corresponding to the movement of the living body in a range irradiated with the signal 56*a* (and 56*b*).

The amplifier 18*a* (and 18*b*) amplifies signal S0*a* (and S0*b*). The filter 20*a* (and 20*b*) is a low-pass filter and filters the amplified signal, for example, having a higher frequency than a signal of the biological vibration. The filters 20*a* and 20*b* are analog filters and cannot completely remove a signal of a frequency to be suppressed. However, by providing the filters 20*a* and 20*b*, the repetitive noise in the A/D converters 22*a* and 22*b* can be suppressed. Further, by limiting the frequency band in the signals S1*a* and S1*b*, a processing load of the processing unit 30 is reduced. The filters 20*a* and 20*b* may be digital filters. The A/D converter 22*a* (and 22*b*) converts the filtered signal S0*a* (and S0*b*) into a signal S1*a* (and S1*b*) which is a digital signal.

It is preferable that the configurations of the radar sensor units 11*a* and 11*b* are substantially the same as each other. That is, the output powers of the signals 56*a* and 56*b* are preferably substantially the same as each other, and the gain of the signal from the antenna 12*a* to the filter 20*a* and the gain of the signal from the antenna 12*b* to the filter 20*b* are preferably substantially the same as each other. In a case where the radar sensor units 11*a* and 11*b* have different gains, it is preferable to calibrate the difference in gain in advance.

The sensor 21 is a vibration sensor, detects vibration of the substrate, for example, and outputs a signal S0*c*. The A/D converter 22*c* converts the signal S0*c* into a signal S1*c* which is a digital signal. At least one of an amplifier and a filter may be provided between the sensor 21 and the A/D converter 22*c*.

The processing unit 30 is, for example, a processor such as a CPU (Central Processing Unit) or a microcomputer, and executes detection processing in cooperation with software. A memory 24 is a non-volatile memory or a volatile memory, and stores setting conditions for detection, data during calculation of information, a program, and the like. An output device 26 outputs the result of the processing by the processing unit 30 to an external device. The external device includes, for example, a display device for displaying an image, an audio device for outputting sound, and a processor different from the processing unit 30. The external device may be a higher-level application in the same processor as the processing unit 30.

Figure 2:
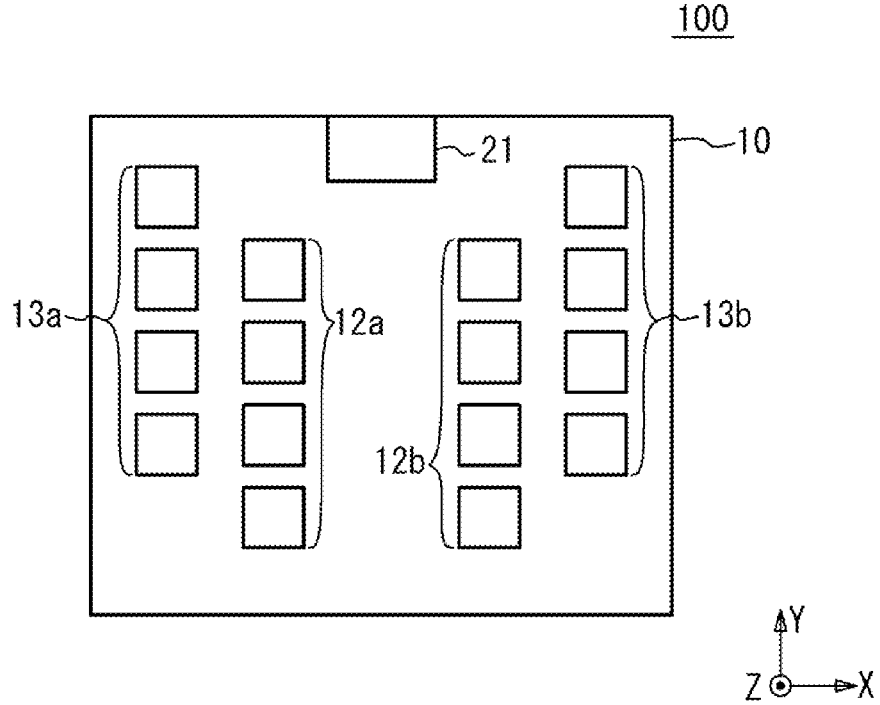
FIG. 2 is a plan view illustrating the detection device according to the first embodiment.

FIG. 2 is a plan view illustrating the detection device according to the first embodiment. A normal direction of the surface of a substrate 10 is defined as a Z direction, and side directions of the substrate 10 are defined as an X direction and a Y direction. As illustrated in FIG. 2, in the detection device 100, the antennas 12*a*, 13*a*, 12*b* and 13*b* and the sensor 21 are provided on the substrate 10. Each of the antennas 12*a*, 13*a*, 12*b* and 13*b* has four antennas arranged in the Y direction, for example. Each of the antennas 12*a*, 13*a*, 12*b* and 13*b* may be a single antenna or an antenna arranged in an array. By disposing a plurality of antennas, the directivity of the antenna can be enhanced. A patch antenna can be used as the antenna, for example.

The sensor 21 is an accelerometer, for example, and detects the vibration of the substrate 10. The high frequency circuits 16*a* and 16*b*, the amplifiers 18*a* and 18*b*, the filters 20*a* and 20*b*, the A/D converters 22*a*, 22*b* and 22*c*, the processing unit 30, the memory 24 and the output device 26 may be provided on a front side (+Z side) or a back side (−Z side) of the substrate 10.

Figure 3:
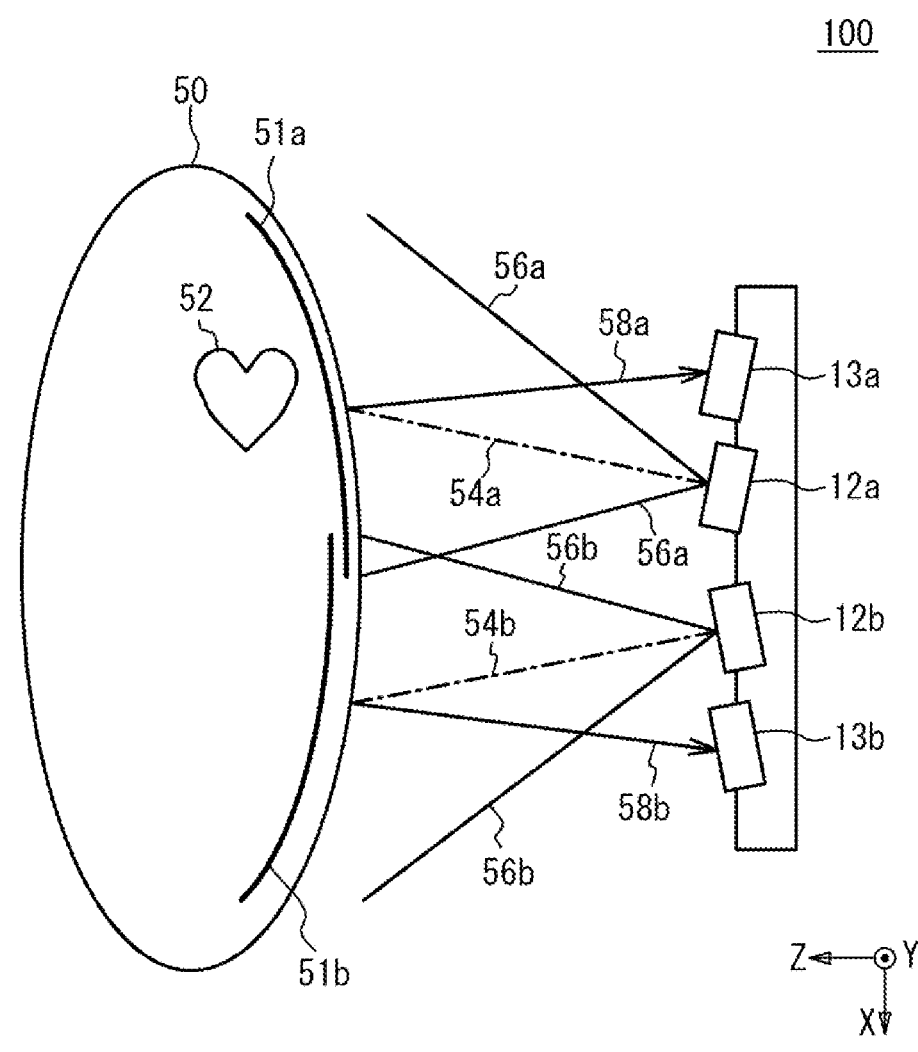
FIG. 3 is a diagram illustrating a use state of the detection device according to the first embodiment.

FIG. 3 is a diagram illustrating a use state of the detection device according to the first embodiment. FIG. 3 illustrates a cross section of a living body 50 such as a human body, and a heart 52 as viewed from a head side. The antennas 12*a* and 13*a* are inclined toward the −X side from a +Z plane of the substrate 10. Thus, a center line 54*a* of the signal 56*a* transmitted by the antenna 12*a* is inclined toward the −X side from the Z direction. Therefore, the signal 56*a* is irradiated to a range 51*a* (left chest) of the −X side of the living body 50, where the heart 52 is located. The antenna 13*a* receives the reflected signal 58*a* in the range 51*a*. The antennas 12*b* and 13*b* are inclined toward the +X side from the +Z plane of the substrate 10. Thus, a center line 54*b* of the signal 56*b* transmitted by the antenna 12*b* is inclined toward the +X side from the Z direction. Therefore, the signal 56*b* is irradiated to a range 51*b* (right chest) of the +X side of the living body 50, where the heart 52 is not located. The antenna 13*b* receives the reflected signal 58*b* in the range 51*b*. In addition, even if the antennas 12*a*, 13*a*, 12*b* and 13*b* are not inclined, desired directivity can be obtained by mounting the antennas 12*a*, 13*a*, 12*b* and 13*b* on a main plane of the substrate 10 and appropriately arranging the plurality of antenna patterns as each antenna.

By mixing the signals 56*a* and 58*a* as illustrated in FIG. 1, the signal S0*a* output from the high frequency circuit 16*a* becomes information on the movement of the range 51*a* of the living body 50. Since the range 51*a* is close to the heart 52, the signal S0*a* is a signal including the vibration of the heartbeat. By mixing the signals 56*b* and 58*b*, the signal S0*b* output from the high frequency circuit 16*b* becomes information on the movement of the range 51*b* of the living body 50. Since the range 51*b* is far from the heart 52, the signal S0*b* does not include the vibration of the heartbeat or becomes a signal with small vibration of the heartbeat.

Although the frequencies of the signals 56*a* and 56*b* may be the same as each other, it is preferable that the frequencies of the signals 56*a* and 56*b* differ from each other by a frequency of vibration or more when there is a possibility of occurrence of interference such as when the signal 58*a* is received by the antenna 13*b* and the signal 58*b* is received by the antenna 13*a*. More specifically, it is preferable that the frequencies of the signals 56*a* and 56*b* are separated from each other by several tens MHz or more.

Figures 4A, 4B:
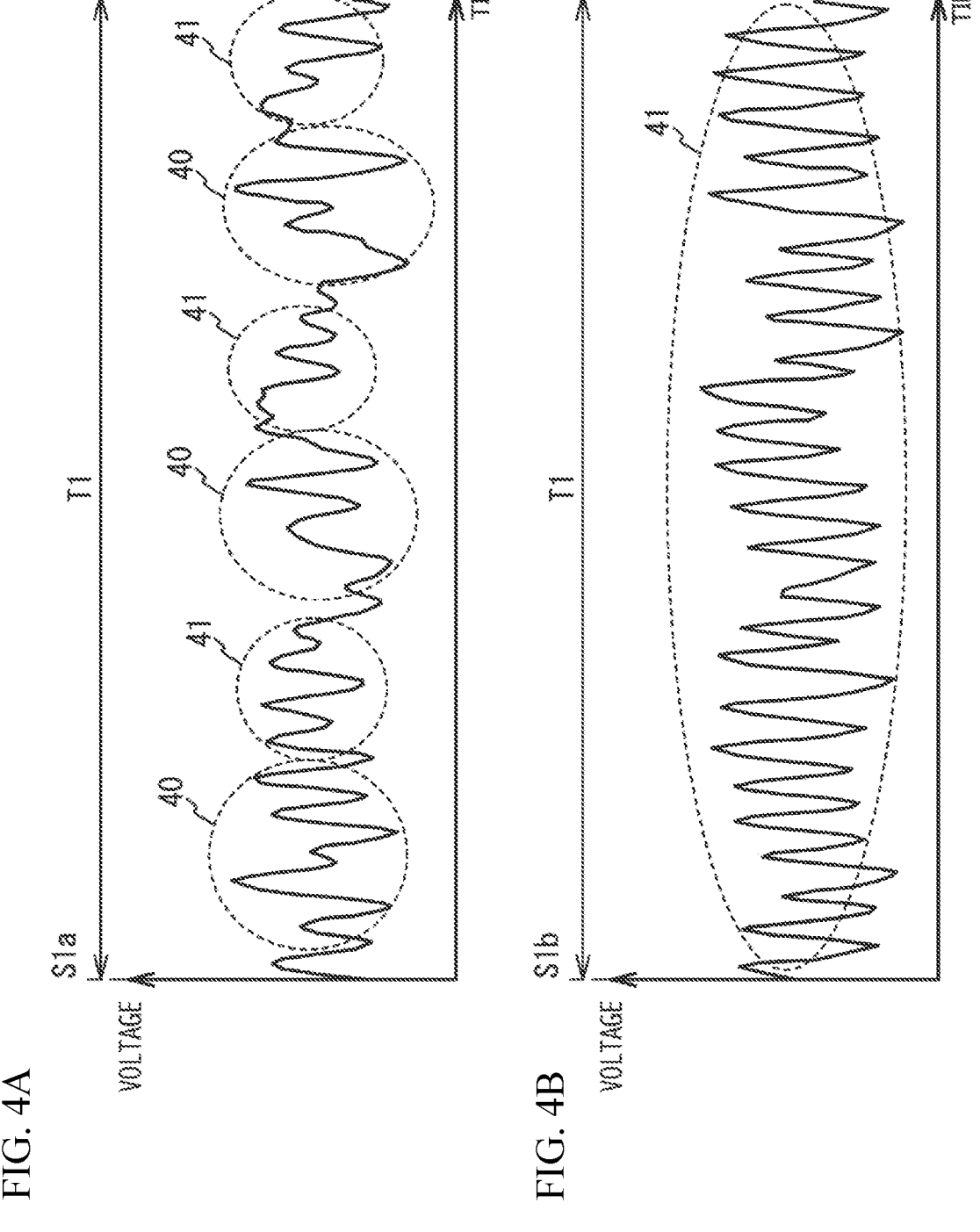
FIGS. 4A and 4B are diagrams illustrating voltages with respect to time indicating examples of signals S1a and S1b, respectively.

FIGS. 4A and 4B are diagrams illustrating voltages with respect to time indicating examples of signals S1*a* and S1*b*, respectively. FIG. 4A and FIG. 4B illustrate signals of a same period T1. In the signals S1*a* and S1*b*, the filters 20*a* and 20*b* suppress signals having frequencies higher than the vibrations of the living body. As illustrated in FIG. 4A, the signal S1*a* includes signals 40 and 41. The signal 40 mainly relates to the vibration of the heartbeat. The signal 41 is mainly a vibration of the living body 50 (for example, respiration) other than the heartbeat and a vibration of a body other than the living body (for example, a vehicle). As illustrated in FIG. 4B, the signal S1*b* hardly includes the signal 40 and is mostly the signal 41.

Figures 5A, 5B:
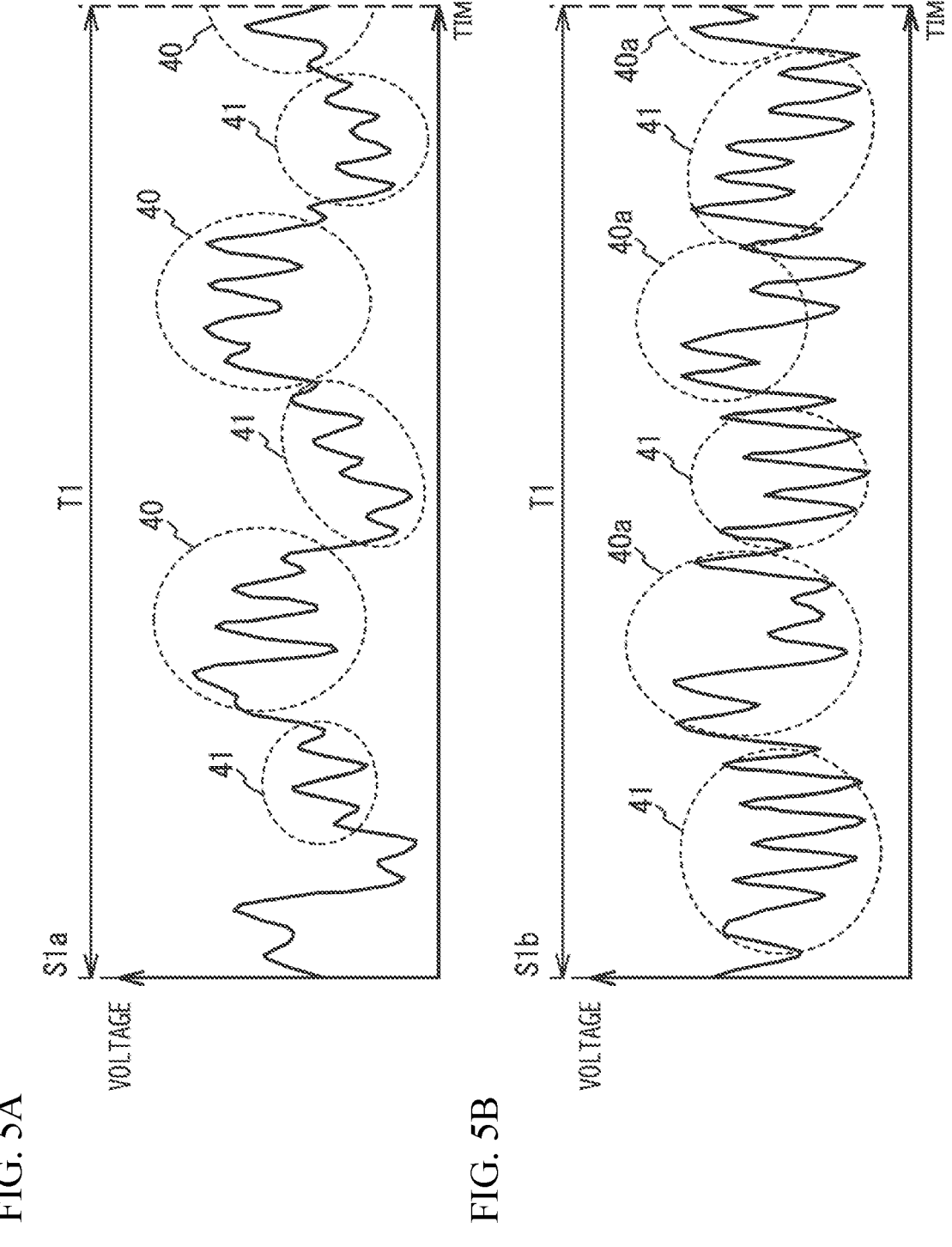
FIGS. 5A and 5B are diagrams illustrating voltages with respect to time indicating examples of signals S1a and S1b, respectively.

FIGS. 5A and 5B are diagrams illustrating voltages with respect to time indicating examples of the signals S1*a* and S1*b*, respectively. FIGS. 5A and 5B illustrate examples in which the directivity of the antenna is lower than the directivity of the antenna of FIGS. 4A and 4B. As illustrated in FIG. 5A, similarly to FIG. 4A, the signal S1*a* includes the signal 40 relating to the vibration of the heartbeat and the signal 41 relating to the vibration other than the heartbeat. As illustrated in FIG. 5B, the signal S1*b* includes, in addition to the signal 41, a signal 40a relating to the vibration of the heartbeat and the vibration other than the heartbeat. As described above, when the directivity of the antenna is low, the signal S1*b* may include the signal relating to the vibration of the heartbeat.

Figure 6:
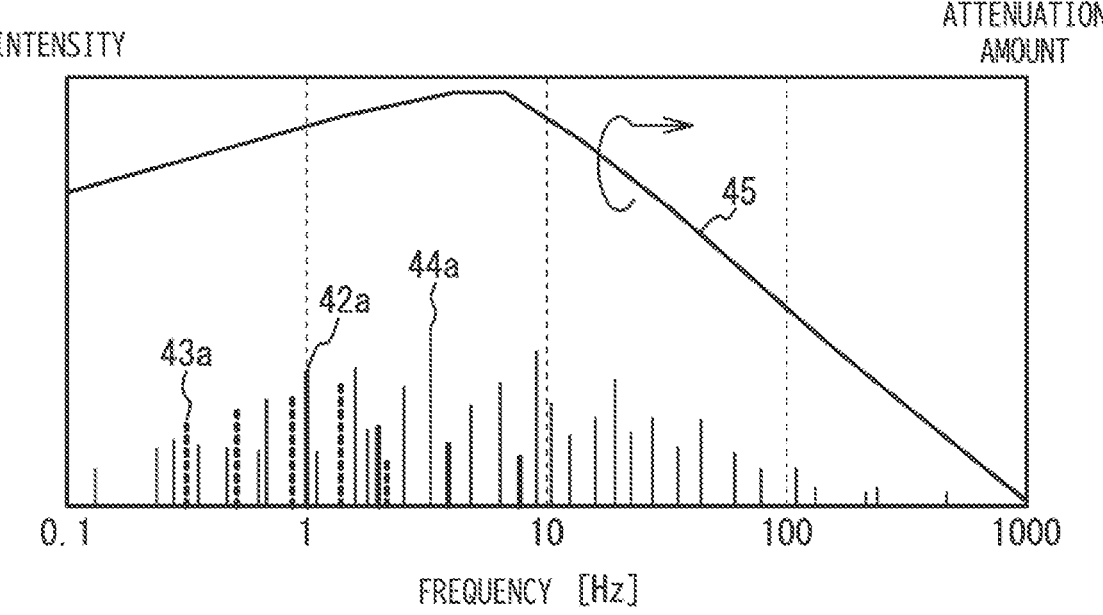
FIG. 6 is a diagram illustrating a spectrum of the signal S1a and a pass characteristic of a filter.

FIG. 6 is a diagram illustrating a spectrum of the signal S1*a* and a pass characteristic of the filter 20a. The spectrum of the signal S1*a* corresponds to a signal after Fourier transformation of the signal S1*a*. A position of the horizontal axis of a line extending in the vertical direction indicates a frequency of the spectrum, and a height in the vertical direction indicates an intensity of the frequency spectrum. A signal 42a is represented by a thick solid line, a signal 43a is represented by a thick dotted line, and a signal 44a is represented by a thin solid line. In a pass characteristic of the filter 20a, the horizontal axis corresponds to the frequency, and the vertical axis corresponds to an attenuation amount by the filter 20a. That is, in the case of a signal having a frequency at which the pass characteristic 45 is small, the attenuation amount of the signal is large due to the filter 20a. In this example, an analog filter is used as the filter 20a. In the analog filter, since the steepness at the cutoff frequency is low, a signal having a frequency of 10 Hz or more also passes through, and the attenuation amount increases as the frequency becomes higher.

The signal 42a is a signal relating to the vibration of the heartbeat. The signal 43a is a signal relating to the vibration of the respiration. The signal 44a is a signal relating to a vibration other than the vibration of the living body, for example, a signal relating to the vibration of the vehicle. Examples of signal 44a are natural vibrations of a spring such as a suspension when the vehicle is an automobile or train, vibrations of air acting like a spring when the vehicle is an airplane, and/or natural vibrations of a spring or the like in a cushion.

Each of the signals 42a and 43a includes a fundamental wave and harmonic waves. Therefore, a plurality of peaks exist in the frequency spectrum of each of the signals 42a and 43a. The frequency of the vibration of the heartbeat is, for example, 1 Hz to 4 Hz. When including the harmonic waves, the frequency of the signal 42a is, for example, 1 Hz to 15 Hz. The frequency of the vibration of the respiration is, for example, 0.3 Hz to 3 Hz. When including the harmonic waves, the frequency of the signal 43a is 0.3 Hz to 10 Hz. The filter 20a suppresses the signal 44a having a frequency higher than 10 Hz, that is, a frequency unrelated to the biological signal. Therefore, as the frequency becomes higher, the frequency spectrum of the signal 44a becomes smaller.

Figure 7:
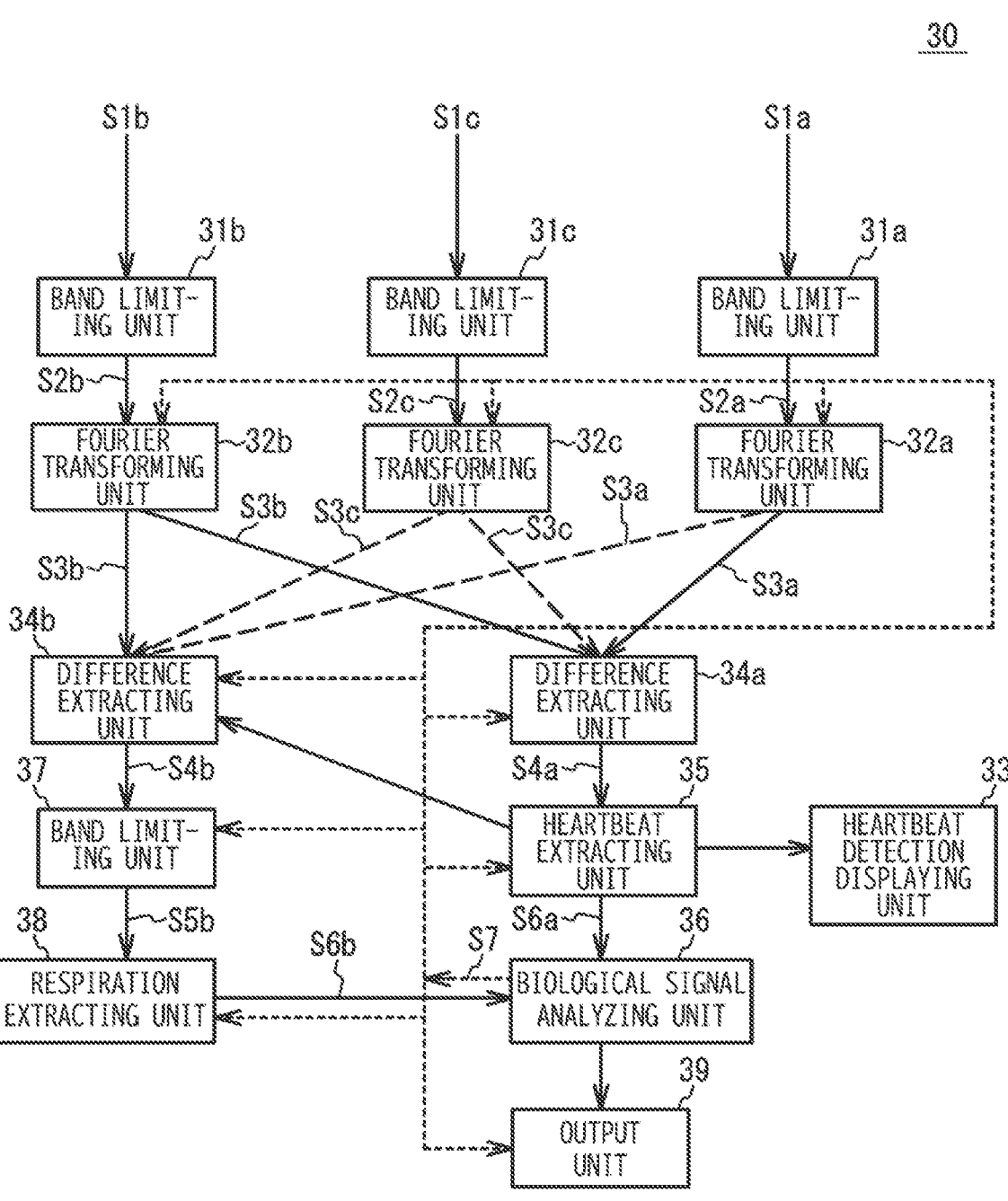
FIG. 7 is a functional block diagram illustrating processing performed by a processing unit in the first embodiment.

FIG. 7 is a functional block diagram illustrating processing performed by the processing unit 30 in the first embodiment. Band limiting units 31a, 31b and 31c limit frequency bands other than the frequency bands of the biological vibrations of signals S1*a*, S1*b* and S1*c*, respectively. The frequency bands of the signals 42a and 43a are, for example, 0.3 Hz to 15 Hz. Therefore, the band limiting units 31a, 31b and 31c remove signals in the frequency band other than the frequency band of 0.2 Hz to 20 Hz, for example, from the signals S1*a*, S1*b* and S1*c*, respectively. Thereby, signals S2*a*, S2*b* and S2*c* output from the band limiting units 31a, 31b and 31c become signals in almost the frequency band of the biological vibration. In this way, by limiting the frequency band not used for subsequent processing, a load of subsequent processing can be reduced. The band limiting units 31a, 31b and 31c may not be provided.

Fourier transforming units 32a, 32b and 32c perform Fourier transformation on the signals 52a, S2*b* and S2*c*, respectively. The Fourier-transformed signals are output as signals S3*a*, S3*b* and S3*c*, respectively. For example, a Fast Fourier Transform (FET) method is used for the calculation of the Fourier transformation.

Figures 8A, 8B, 8C:
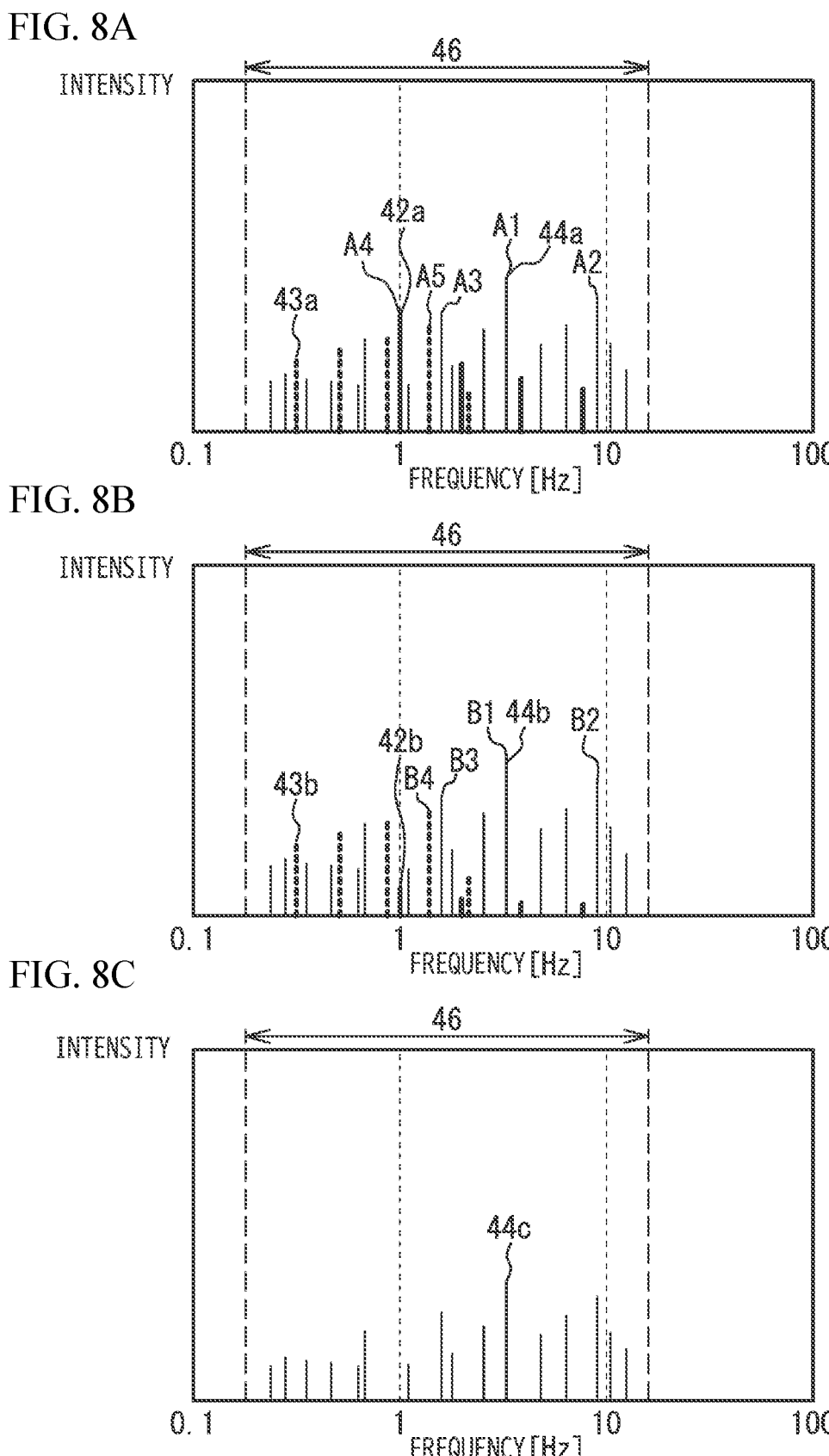
FIGS. 8A to 8C are diagrams illustrating the spectra of signals S3a, S3b and S3c.

FIGS. 8A to 8C are diagrams illustrating the spectra of the signals S3*a*, S3*b* and S3*c*, respectively. A position of the horizontal axis of a line extending in the vertical direction indicates the frequency of the spectrum, and a height in the vertical direction indicates an intensity of the frequency spectrum. Signals 42a and 42b are represented by thick solid lines, signals 43a and 43b are represented by thick dotted lines, and signals 44a, 44b and 44c are represented by thin solid lines.

As illustrated in FIG. 8A, the band limiting unit 31a removes signals in a band other than a band 46 from the signal S1*a* from the range 51a close to the heart 52 in FIG. 3. Therefore, the signal S3*a* is a signal having frequencies almost within the band 46 with respect to the signal S1*a* in FIG. 6.

As illustrated in FIG. 8B, the band limiting unit 31b removes signals in a band other than the band 46 from the signal S1*b* from the range 51b far from the heart 52 in FIG. 3. Therefore, the signal S3*b* is a signal having frequencies almost within the band 46. In the signal S3*b*, the signal 42b relating to the vibration of the heartbeat is lower than the signal 42a relating to the vibration of the heartbeat in the signal S3*a*. This is because, as illustrated in FIGS. 4B and 5B, the signal S1*b* hardly includes the signal 40 relating to the vibration of the heartbeat. The signal S3*b* includes the signal 43b relating to the vibration of the respiration and the signal 44b relating to the vibration other than the vibration of the living body to the same extent as the signals 43a and 44a in the signal S3*a*.

Comparing FIG. 8A with FIG. 8B, the signals 43a and 43b relating to the respiration have substantially the same frequency and the same intensity. This is because, as illustrated in FIG. 3, the ranges 51a and 51b correspond to a left chest and a right chest of the living body 50, respectively, so that the vibration of the respiration is almost the same in the ranges 51a and 51b. The signals 44a and 44b relating to the vibrations other than the vibrations of the living body have substantially the same frequency and the same intensity. This is because the vibrations of the vehicle transmitted to the living body 50 are substantially the same, and the vibrations in the ranges 51a and 51b are detected using the radar sensor units 11a and 11b having substantially the same configuration.

As illustrated in FIG. 8C, the band limiting unit 31c removes signals in a band other than the band 46 from the signal S1*c*. For this reason, the signal S3*c* is a signal which hardly includes signals in the band other than the band 46. The signal S3*c* is almost the signal 44c relating to the vibration other than the vibration of the living body, and hardly includes the signal relating to the vibration of the living body 50.

The intensity of the signal 44c in FIG. 8C differs from the intensities of the signals 44a and 44b in FIGS. 8A and 8B. This is because the intensity of the vibration transmitted to the living body 50 and the intensity of the vibration transmitted to the substrate 10 are not equal to each other.

A difference extracting unit 34a extracts a difference between the signal S3*a* and the signal S3*b*, and removes signals present in both the signals S3*a* and S3*b*. For example, in FIG. 8A, signals having higher intensities are designated as signals A1, A2, A3, A4 and A5 in order. In FIG. 8B, signals having higher intensities are designated as signals B1, B2, B3, and B4 in order. The difference extracting unit 34a removes the signal A1 from the signal S3*a* when the frequencies of the signals A1 and B1 having the highest intensity are the same as each other. Next, the difference extracting unit 34a removes the signal A2 from the signal S3*a* when the frequencies of the signals A2 and B2 are the same as each other. Similarly, the difference extracting unit 34a removes the signal A3 from the signal S3*a*. The frequencies of signals A4 and B4 does not match. Therefore, the difference extracting unit 34a does not remove the signal A4 from the signal S3*a*. Next, when the frequencies of the signals A5 and B4 are the same as each other, the difference extracting unit 34a removes the signal A5 from the signal S3*a*. Thus, the signals 43a and 44a are removed from the signal S3*a*. The difference extracting unit 34a outputs the processed signal as a signal S4*a*. The difference extracting unit 34a may remove, from the signal S3*a*, a frequency spectrum having a frequency matching a frequency whose intensity is greater than or equal to a predetermined value in the frequency spectrum of the signal S3*b*. Further, the difference extracting unit 34a may remove a frequency spectrum having an intensity equal to or less than a predetermined value from at least one of the signal S3*a* and the signal S3*b* before the difference extraction.

The difference extracting unit 34a may remove the signal 44a by using the signal S3*c* in addition to the signal S3*a*. Accordingly, the signal 44a can be more appropriately removed.

A heartbeat extracting unit 35 synthesizes the waveform of the time axis from the signal S4*a* to generate the waveform of the vibration of the heartbeat in the period T1. The heartbeat extracting unit 35 outputs the generated waveform as a signal S6*a*.

A heartbeat detection displaying unit 33 causes the output device 26 to output whether the waveform of the vibration of the heartbeat is synthesized in the heartbeat extracting unit 35. For example, when the output device 26 is a display, the heartbeat detection displaying unit 33 causes the output device 26 to display a heart rate and the like. When the output device 26 is a light or a speaker, the heartbeat detection displaying unit 33 blinks the light or outputs sound in synchronization with the heartbeat. When the heartbeat extracting unit 35 cannot synthesize the waveform of the vibration of the heartbeat, the range 51a may be deviated from the position of the heart 52. If the output device 26 indicates that the heartbeat could not be detected, a user can adjust a mounting position of the substrate 10 such as changing the mounting position of the substrate 10 so that the heartbeat can be detected.

A difference extracting unit 34b extracts a difference between the signal S3*b* and the signal S3*c*, and removes signals present in both the signals S3*b* and S3*c*. Thus, the signal 44b in FIG. 8b can be removed. When the signal 42b is included in the signal S3*b*, the difference extracting unit 34b may receive the signal S4*a* from the heartbeat extracting unit 35 and may remove the signal 42b from the signal S3*b* using the signal S4*a*. The difference extracting unit 34b outputs the processed signal as a signal S4*b*.

When the signal 42b is included in the signal S4*b*, a band limiting unit 37 limits the band so as to remove the signal 42b. For example, in FIG. 8B, the signal 42b can be removed by removing a signal having a frequency of 1 Hz or more. The band limiting unit 37 outputs the processed signal as a signal S5*b*. The band limiting unit 37 may not be provided.

A respiration extracting unit 38 synthesizes the waveform of the time axis from the signal S5*b* to generate the waveform of the vibration of the respiration in the period T1. The respiration extracting unit 38 outputs the generated waveform as a signal S6*b*. A biological signal analyzing unit 36 analyzes the signals S6*a* and S6*b*. An output unit 39 outputs an analysis result.

The biological signal analyzing unit 36 outputs a signal S7 for synchronizing the periods during which the Fourier transforming units 32a, 32b and 32c, the difference extracting units 34a and 34b, the heartbeat extracting unit 35, the band limiting unit 37, the respiration extracting unit 38, and the output unit 39 operate. The Fourier transforming units 32a, 32b and 32c perform Fourier transformation based on the synchronization signal. Therefore, the periods for Fourier transformation of the signals S1*a*, S1*b* and S1*c* are substantially equal to each other. The period of the Fourier transformation is, for example, the period T1 illustrated in FIGS. 4A to 5B.

Figure 9:
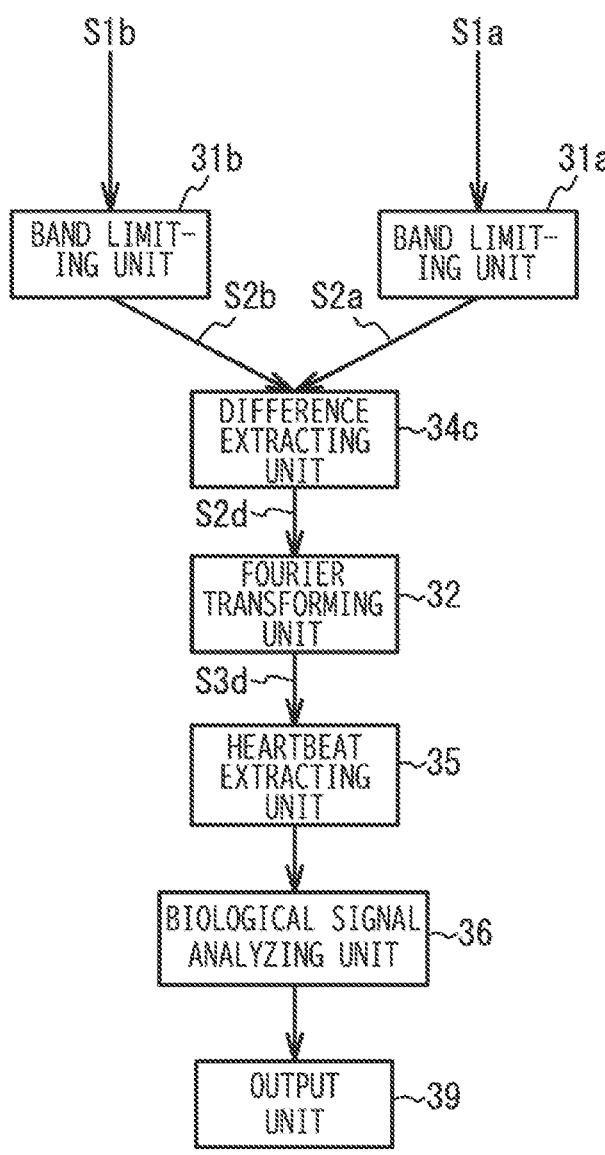
FIG. 9 is another example of a functional block diagram illustrating processing performed by the processing unit in the first embodiment.

FIG. 9 is another example of a functional block diagram illustrating processing performed by the processing unit 30 in the first embodiment. As illustrated in FIG. 9, in this example, the sensor 21 is not provided and the signal S1*c* is not input to the processing unit 30. A difference extracting unit 34c performs difference processing between the signal S2*a* output from the band limiting unit 31a and the signal S2*b* output from the band limiting unit 31b. The difference extracting unit 34c subtracts S2*b* from the signal S2*a*, for example, whereby the waveform of FIG. 4B is subtracted from the waveform of FIG. 4A, for example. Therefore, a signal S2*d* output from the difference extracting unit 34c is mainly a signal relating to the vibration of the heartbeat. A Fourier transforming unit 32 performs Fourier transformation on the signal S2*d* and outputs a signal S3*d*. The processes of the heartbeat extracting unit 35, the biological signal analyzing unit 36, and the output unit 39 in FIG. 9 are the same as those in FIG. 7, and description thereof is omitted.

As illustrated in FIG. 9, the difference extracting unit 34c may extract the difference between the signal S2*a* and the signal S2*b* before the Fourier transformation, and the Fourier transforming unit 32 may perform the Fourier transformation on the difference extracted signal S2*d*. Accordingly, the signals 43a and 44a can be appropriately removed.

Figure 10A:
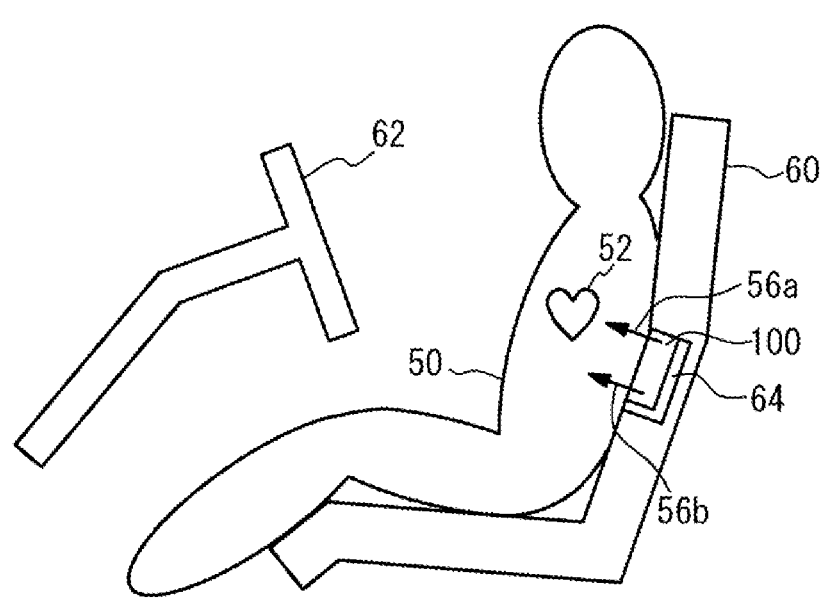
FIGS. 10A and 10B are diagrams illustrating an example of mounting the detection device on a vehicle.
Figure 11A:
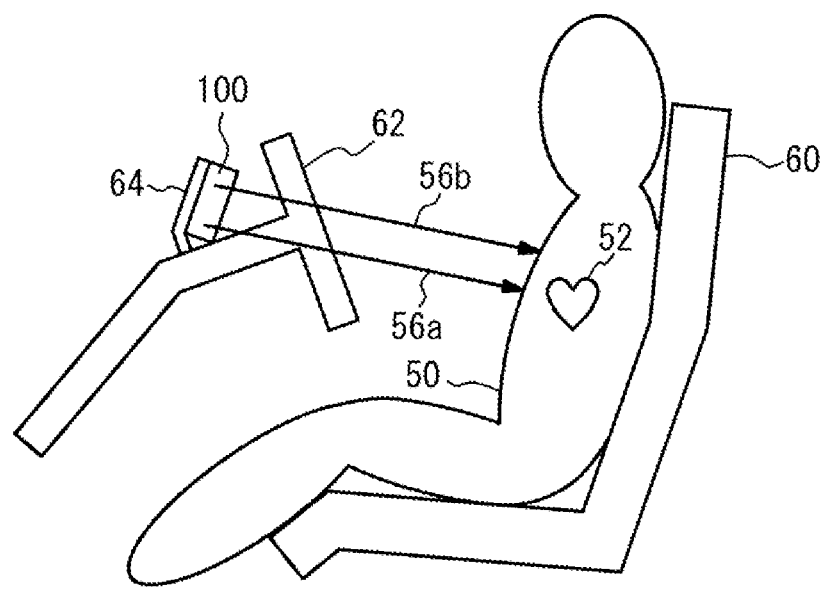
FIGS. 11A and 11B are diagrams illustrating an example of mounting the detection device on the vehicle.
Figure 11B:
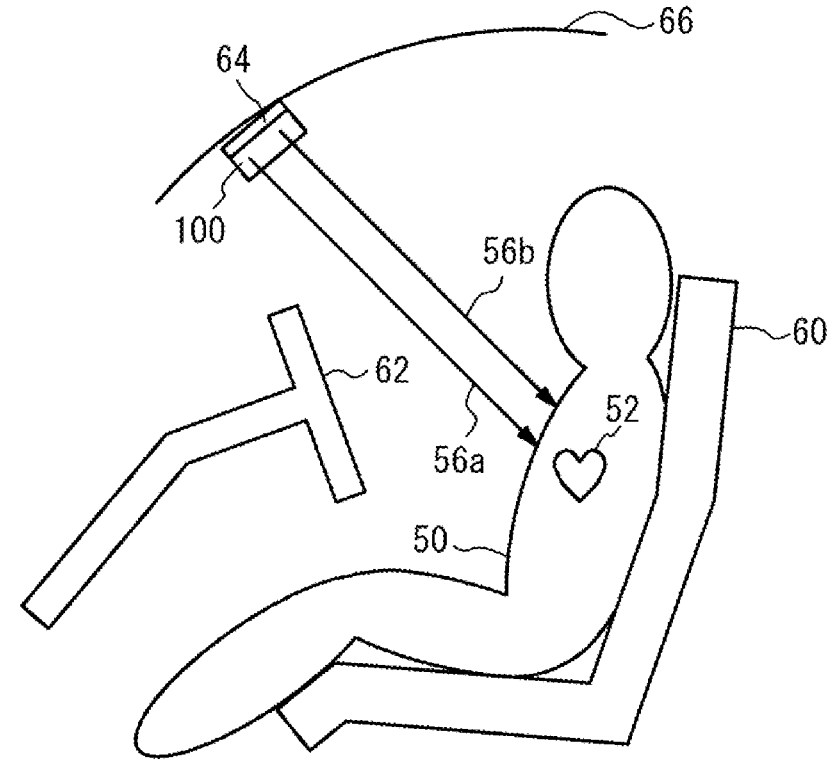

FIGS. 10A and 11B are diagrams illustrating an example of mounting the detection device 100 on a vehicle. As illustrated in FIG. 10A, a seat 60 and a handle 62 are provided in the vehicle. The detection system includes the detection device 100 and a mounting member 64. The detection device 100 is mounted in the seat 60 by the mounting member 64. The detection device 100 irradiates the signals 56a and 56b to the living body 50 in a space. The signal 56a is irradiated toward the back of the living body 50 near the heart 52, and the signal 56b is irradiated toward the back of the living body 50 away from the heart 52.

Figure 10B:
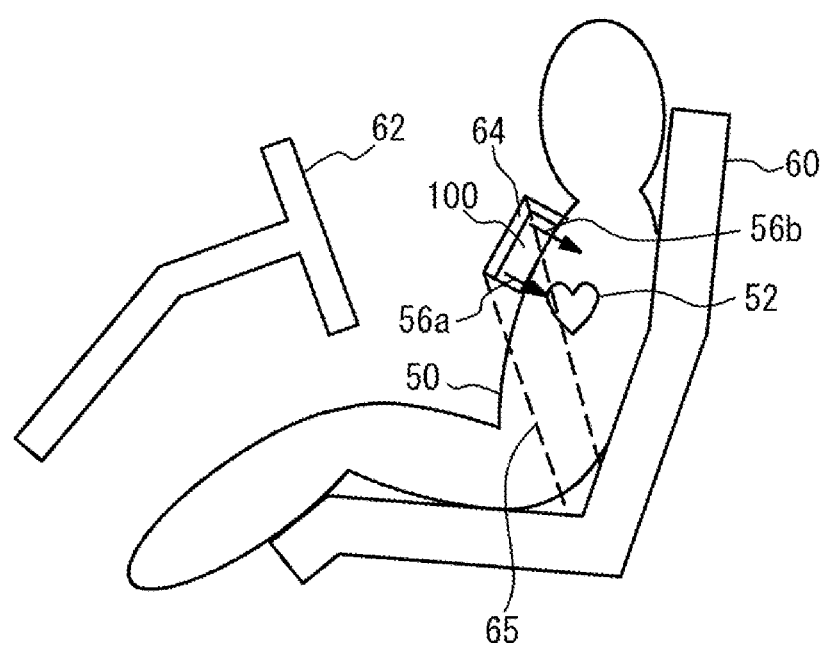

As illustrated in FIG. 10b, the detection device 100 is mounted on a seat belt 65 by the mounting member 64. The detection device 100 may be mounted on a card holder suspended from the neck of a person. The signal 56a is irradiated to the chest of the living body 50 near the heart 52, and the signal 56b is irradiated to the chest of the living body 50 away from the heart 52.

As illustrated in FIG. 11A, the detection device 100 is mounted on the dashboard or console near the handle 62 by the mounting member 64. The signal 56a is irradiated to the chest of the living body 50 near the heart 52, and the signal 56b is irradiated to the chest of the living body 50 away from the heart 52.

As illustrated in FIG. 11B, the detection device 100 is mounted on a ceiling 66 or a sun visor by the mounting member 64. The signal 56a is irradiated to the chest of the living body 50 near the heart 52, and the signal 56b is irradiated to the chest of the living body 50 away from the heart 52.

In FIGS. 10A and 10B, since the detection device 100 can be mounted near the living body 50, the reflection of the signals 56a and 56b by metal or the like can be suppressed. Further, since the passenger sits at almost the same position on the seat, it is not necessary to adjust an irradiation direction of the signals 56a and 56b.

According to the first embodiment, as illustrated in FIGS. 1 and 3, the radar sensor unit 11a (first sensor) transmits the signal 56a (first electromagnetic wave) to the range 51a (first range) of the living body 50 and receives the signal 58a reflected in the range 51a. The radar sensor unit 11b (second sensor) transmits the signal 56b (second electromagnetic wave) to the range 51b (second range different from the first range) of the living body 50, and receives the signal 58b reflected in the range 51b. The processing unit 30 (calculation unit) calculates information on the living body 50 (for example, information on the heartbeat) based on the signal S1a (first signal) output from the radar sensor unit 11a and the signal S1b (second signal) output from the radar sensor unit 11b. In this way, by using the signals of the radar sensor units 11a and 11b, it is possible to remove noise caused by the vibration of a vehicle or the like and to calculate information on the living body 50.

By making the range 51a closer to the heart 52 than the range 51b, the signal 40 relating to the vibration of the heartbeat included in the signal S1b becomes smaller than the signal S1a as illustrated in FIGS. 4A to 5B. Therefore, by using the signals S1a and S1b, the processing unit 30 can calculate the information on the heartbeat of the living body 50. By defining the range 51a as the left chest and the range 51b as the right chest, the vibrations other than the vibrations of the heartbeat in the ranges 51a and 51b are substantially the same as each other. Therefore, the processing unit 30 can calculate the information on the heartbeat of the living body 50 with high accuracy. The range 51b may be the neck or abdomen or the like. Further, by defining the range 51a as a portion with an artery and the range 51b as a portion without an artery, the processing unit 30 can calculate information on the pulse of the living body. It is preferable that the ranges 51a and 51b are located close to each other from the viewpoint that the vibrations other than the heartbeat or the pulse in the ranges 51a and 51b are substantially the same as each other. Vibrations such as the heartbeat, the pulse, and the respiration in different ranges of the living body 50 are considered to be different from each other. Therefore, if the ranges 51a and 51b are different ranges in the living body 50, the processing unit 30 can calculate information on, for example, the heartbeat, the pulse or the respiration of the living body 50. In the first embodiment, the living body 50 of a human is described as an example, but a living body of a pet may be used.

As illustrated in FIG. 7, the processing unit 30 calculates the information on the living body 50 based on the signal S3a (third signal) obtained by performing the Fourier transformation on the signal S1a and the signal S3b (fourth signal) obtained by performing the Fourier transformation on the signal S1b. As illustrated in FIGS. 8A and 8B, the processing unit 30 compares the frequencies in the frequency spectrum of the signal S3a with the frequencies in the frequency spectrum of the signal S3b, for example, and calculates the information on the living body 50 based on a comparison result. More specifically, when the frequencies in the frequency spectrum of the signal S3b substantially match the frequencies in the frequency spectrum of the signal S3a, a frequency spectrum whose frequencies substantially match is removed from the signal S3a. Thus, a signal having a common frequency can be removed in the signals S3a and S3b.

As illustrated in FIG. 9, the processing unit 30 may calculate the information on the living body 50 based on the signals S2a and S2b before the Fourier transformation. The processing unit 30 may calculate the signal relating to the living body 50 based on the difference between the signal S2a and the signal S2b, for example.

A first period during which the Fourier transforming unit 32a performs the Fourier transformation on the signal S2a and a second period during which the Fourier transforming unit 32b performs the Fourier transformation on the signal S2b are substantially the same period. That is, the start times of the period T1 in FIGS. 4A and 4B are substantially the same in real time, and the end times thereof are substantially the same in real time. Thus, it is possible to improve the calculation accuracy of the information on the living body 50. It should be noted that the first period and the second period are substantially the same as each other means that the first period and the second period are the same as each other to such an extent that no error occurs in the processing of the processing unit 30.

The antennas 12a (first transmitting antenna), 13a (first receiving antenna), 12b (second transmitting antenna) and 13b (second receiving antenna) are mounted on the substrate 10 (base body). The sensor 21 (third sensor) detects vibration of the substrate 10. The processing unit 30 calculates the information on the living body 50 based on the signal S1c (fifth signal) output from the sensor 21. As a result, the calculation accuracy of the information on the living body 50 can be improved. The process using the sensor 21 is an auxiliary process, and the process using the sensor 21 may not be performed. That is, in FIGS. 1 and 7, the vibration sensor unit 11c, the band limiting unit 31c and the Fourier transforming unit 32c may not be provided.

In FIG. 7, the processing unit 30 calculates the information on the vibration of the respiration, but may not calculate the information on the vibration of the respiration. That is, the difference extracting unit 34b, the band limiting unit 37 and the respiration extracting unit 38 may not be provided.

The heartbeat detection displaying unit 33 outputs whether the information on the living body has been calculated. Thus, the user can know whether the ranges 51a and 51b are appropriate. If the ranges 51a and 51b are not appropriate, the ranges 51a and 51b can be adjusted. The heartbeat detection displaying unit 33 may not be provided.

In the first embodiment, the information on the living body 50 is detected by a Doppler system. Other methods such as an FM-CW (Frequency Modulated Continuous Wave) method may be used to detect the information on the living body 50. Further, an object to which the signals 56a and 56b are irradiated may be other than the living body, and the processing unit 30 may calculate information on the object to which the signals 56a and 56b are reflected.

As illustrated in FIGS. 10A to 11B, the mounting member 64 mounts the detection device 100 such that the range 51a is closer to the heart 52 than the range 51b. Thus, the processing unit 30 can calculate the information on the heartbeat with high accuracy. The mounting member 64 mounts the detection device on the vehicle. Thereby, the information on the living body 50 can be calculated with high accuracy even if the vehicle vibrates. In FIGS. 10A to 11B, the vehicle such as the automobile is described as an example of the vehicle, but the vehicle may be the train or airplane. The vehicle occupant may be a driver or a passenger. From the viewpoint of safe operation of vehicles, there are cases in which information on the driver's body is managed. For example, a mental state, sleepiness, arrhythmia or cardiac arrest in the health conditions of the driver is managed. When the driver is in a serious state, a warning or notification or automatic stop of operation is performed, whereby a serious accident can be prevented in advance. In such a case, it is preferable to calculate information on the living body of the driver.

All examples and conditional language provided herein are intended for the purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A detection device comprising:
a first sensor including a first transmitting antenna and a first receiving antenna, the first transmitting antenna transmitting a first electromagnetic wave to an object and the first receiving antenna receiving the first electromagnetic wave reflected by the object, the first sensor outputting a first signal corresponding to a difference between the first electromagnetic wave transmitted from the first transmitting antenna and the first electromagnetic wave received by the first receiving antenna;
a second sensor including a second transmitting antenna and a second receiving antenna, the second transmitting antenna transmitting a second electromagnetic wave to the object and the second receiving antenna receiving the second electromagnetic wave reflected by the object, the second sensor outputting a second signal corresponding to a difference between the second electromagnetic wave transmitted from the second transmitting antenna and the second electromagnetic wave received by the second receiving antenna;
a base body having a front side and a back side, on which the first sensor and the second sensor are mounted on the front side;
an accelerometer that detects vibration of the base body, and outputs a third signal corresponding to detected vibration; and
a processor that extracts a first difference between the first signal output from the first sensor and the second signal output from the second sensor, and a second difference between the second signal output from the second sensor and the third signal output from the accelerometer, and outputs the first difference and the second difference as information on the object reflecting the first electromagnetic wave and the second electromagnetic wave,
wherein the first sensor is arranged on the front side of the base body so that the first electromagnetic wave is directed to a first range of the object, and the second sensor is arranged on the front side of the base body so that the second electromagnetic wave is directed to a second range different from the first range of the object, and
wherein when the object is a living body, the processor generates heartbeat information of the living body based on the first difference and generates respiration information of the living body based on the second difference.

2. The detection device according to claim 1, wherein the processor extracts the first difference based on a fourth signal obtained by performing Fourier transformation on the first signal, and a fifth signal obtained by performing Fourier transformation on the second signal.

3. The detection device according to claim 2, wherein the processor compares a frequency spectrum of the fourth signal and a frequency spectrum of the fifth signal, and extracts the first difference based on a comparison result.

4. A detection system including a detection device mounted on a vehicle and detecting information on a living body in the vehicle, the detection device comprising:
a first sensor including a first transmitting antenna and a first receiving antenna, the first transmitting antenna transmitting a first electromagnetic wave to the living body and the first receiving antenna receiving the first electromagnetic wave reflected by the living body, the first sensor outputting a first signal corresponding to a difference between the first electromagnetic wave transmitted from the first transmitting antenna and the first electromagnetic wave received by the first receiving antenna;
a second sensor including a second transmitting antenna and a second receiving antenna, the second transmitting antenna transmitting a second electromagnetic wave to the living body and the second receiving antenna receiving the second electromagnetic wave reflected by the living body, the second sensor outputting a second signal corresponding to a difference between the second electromagnetic wave transmitted from the second transmitting antenna and the second electromagnetic wave received by the second receiving antenna;
a base body having a front side and a back side, on which the first sensor and the second sensor are mounted on the front side;
an accelerometer that detects vibration of the base body, and outputs a third signal corresponding to detected vibration, and
a processor that extracts a first difference between the first signal output from the first sensor and the second signal output from the second sensor, and a second difference between the second signal output from the second sensor and the third signal output from the accelerometer,
wherein the first sensor is arranged on the front side of the base body so that the first electromagnetic wave is directed to a first range of the living body, and the second sensor is arranged on the front side of the base body so that the second electromagnetic wave is directed to a second range different from the first range of the living body, and the first range is closer to a heart of the living body than the second range, and wherein the processor generates heartbeat information of the living body based on the first difference and generates respiration information of the living body based on the second difference.

5. A detection device comprising:

a first sensor including a first transmitting antenna and a first receiving antenna, the first transmitting antenna transmitting a first electromagnetic wave to an object and the first receiving antenna receiving the first electromagnetic wave reflected by the object, the first sensor outputting a first signal corresponding to a difference between the first electromagnetic wave transmitted from the first transmitting antenna and the first electromagnetic wave received by the first receiving antenna;

a second sensor including a second transmitting antenna and a second receiving antenna, the second transmitting antenna transmitting a second electromagnetic wave to the object and the second receiving antenna receiving the second electromagnetic wave reflected by the object, the second sensor outputting a second signal corresponding to a difference between the second electromagnetic wave transmitted from the second transmitting antenna and the second electromagnetic wave received by the second receiving antenna; and a processor that extracts a difference between the first signal output from the first sensor and the second signal output from the second sensor, and outputs the difference as information on the object reflecting the first electromagnetic wave and the second electromagnetic wave, wherein the first sensor is arranged on the front side of the base body so that the first electromagnetic wave is directed to a first range of the object, and the second sensor is arranged on the front side of the base body so that the second electromagnetic wave is directed to a second range different from the first range of the object, and wherein when the object is a living body, the processor generates heartbeat information of the living body based on the difference.

* * * * *